United States Patent
Ibert et al.

(10) Patent No.: US 9,346,819 B2
(45) Date of Patent: May 24, 2016

(54) METHOD OF SYNTHESIS OF A COMPOSITION CONTAINING AT LEAST ONE INTERNAL DEHYDRATION PRODUCT OF A HYDROGENATED SUGAR BY HETEROGENEOUS CATALYSIS

(71) Applicant: ROQUETTE FRERES, Lestrem (FR)

(72) Inventors: Mathias Ibert, La Chapelle D'armentieres (FR); Herve Wyart, Cuinchy (FR); Wolfgang Holderich, Frankenthal/Pfalz (DE); Oana-Alice Rusu P., Vaslui (RO)

(73) Assignee: ROQUETTE FRERES, Lestrem (FR)

( * ) Notice: Subject to any disclaimer, the term of this patent is extended or adjusted under 35 U.S.C. 154(b) by 0 days.

(21) Appl. No.: 14/419,747

(22) PCT Filed: Aug. 7, 2013

(86) PCT No.: PCT/EP2013/066592
§ 371 (c)(1),
(2) Date: Feb. 5, 2015

(87) PCT Pub. No.: WO2014/023789
PCT Pub. Date: Feb. 13, 2014

(65) Prior Publication Data
US 2015/0183796 A1    Jul. 2, 2015

(30) Foreign Application Priority Data
Aug. 8, 2012   (EP) ................................. 12305987

(51) Int. Cl.
*C07D 493/04* (2006.01)

(52) U.S. Cl.
CPC .................................. *C07D 493/04* (2013.01)

(58) Field of Classification Search
CPC ................................................... C07D 493/04
USPC ....................................................... 549/464
See application file for complete search history.

(56) References Cited

U.S. PATENT DOCUMENTS 5,981,812 A    11/1999  Eufinger et al.
7,420,067 B2    9/2008  Sanborn

FOREIGN PATENT DOCUMENTS

| CN | 101 386 610 A | 3/2009 |
| CN | 101 492 457 A | 7/2009 |
| CN | 101 492 458 A | 7/2009 |
| EP | 0 844 227 A2 | 5/1998 |

OTHER PUBLICATIONS

Mingyan Gu et al.: "Metal (IV) Phosphates as Solid Catalysts for Selective Dehydration of Sorbitol to Isosorbide", Catalysis Letters, Kluwer Academic Publishers-Plenum Publishers, NE, vol. 133, No. 1-2, Sep. 2, 2009, pp. 214-220, XP019746855, ISSN: 1572-879X, 001: 10.1007/S10562-009-0142-5 the whole document.

Hutchings G J et al.: "Dehydration of 2-Methylbutanal and Methyl Isopropyl Ketone to Isoprene Using Boron and Aluminium Phosphate Catalysts", Journal of Catalysis, Academic Press, Duluth, MN, US, vol. 188, No. 2, Dec. 10, 1999, pp. 291-299, XP004443016, ISSN: 0021-9517, DOI: 10.1006/JCAT.1999.2620 the whole document.

Ruwet M et al.: "Catalytic reactivity of phosphates with 1-butanol, pure and in a mixture with acetone, ethanol, acetic acid and water", Bulletin Des Societes Chimiques Belges, Louvain [U.A.]: Centerick, BE, vol. 96, No. 4, Jan. 1, 1987, pp. 281-292, XP009092355, ISSN: 0037-9646 the whole document.

Zhen-Chen Tang et al.: "Phosphoric Acid Modified Nb 2 0 5 : A Selective and Reusable Catalyst for Dehydration of Sorbitol to Isosorbide", Bulletin of the Korean Chemical Society, vol. 31, No. 12, Dec. 20, 2010, pp. 3679-3683, XP055044394, ISSN: 0253-2964, DOI: 10.5012/bkcs.2010.31.12.3679 the whole document.

Duclos A et al.: "A Simple Conversion of Polyols Into Anhydroalditols", Synthesis, Georg Thieme Verlag, Stuttgart, DE, vol. 10, Oct. 1, 1994, pp. 1087-1090, XP001056553, ISSN: 0039-7881, DOI: 10.1055/S-1994-25643 the whole document.

Goodwin J C et al.: "Preparation of bicyclic hexitol anhydrides by using acidic cation-exchange resin in a binary solvent. <p13>C-N. m.r. spectroscopy confirms configurational inversion in chloride displacement of methanesulfonate in isomannide and isosorbide derivatives", Carbohydrate Research, Pergamon, GB, vol. 79, No. 1, Feb. 1, 1980, pp. 133-141, XP026622475, ISSN: 0008-6215, DOI: 10.1016/S0008-6215(00)85138-1 [retrieved on Feb. 1, 1980] the whole document.

Fawzia et al.: "Heterogeneous liquid phase catalysis by metal (IV) phosphates of cyclic ether formation and a reverse Prins reaction", Journal of Molecular Catalysis A, Chemical 152 (2000) 187-200.

International Search Report, dated Sep. 3, 2013, from corresponding PCT application.

*Primary Examiner* — Taofiq A Solola
(74) *Attorney, Agent, or Firm* — Young & Thompson

(57) ABSTRACT

A simple, low cost, environmentally friendly and sustainable process for the production of internal dehydration products of hydrogenated sugar, implementing trivalent metal phosphate (metal (III) phosphates) as catalysts during the dehydratation step.

20 Claims, No Drawings

METHOD OF SYNTHESIS OF A COMPOSITION CONTAINING AT LEAST ONE INTERNAL DEHYDRATION PRODUCT OF A HYDROGENATED SUGAR BY HETEROGENEOUS CATALYSIS

FIELD OF THE INVENTION

The invention concerns a novel method for preparing a composition containing at least one internal dehydration product of a hydrogenated sugar, said method comprises a step of dehydration of a hydrogenated sugar in presence of a solid trivalent metal phosphate catalyst.

TECHNICAL BACKGROUND OF THE INVENTION

Internal dehydration products of a hydrogenated sugar belong to the so-called "biomass-derived substances", obtainable from natural products, being classified as "renewable resources".

The expression "hydrogenated sugar" for the purposes of the present invention is understood to mean a sugar alcohol (also known as a polyol, polyhydric alcohol, polyalcohol, or glycitol) which is a hydrogenated form of carbohydrate, wherein a carbonyl group (aldehyde or ketone, reducing sugar) has been reduced to a primary or secondary hydroxyl group (hence the alcohol). Examples of hydrogenated sugars include in particular: (i) hexitols such as, for example, sorbitol, mannitol, iditol and galactitol, (ii) pentitols such as, for example, arabitol, ribitol and xylitol, (iii) tetritols such as, for example, erythritol and threitol.

The expression "internal dehydration product" is understood to mean any product resulting, in any manner, in one or more steps, from removal of one or more molecules of water from the original internal structure of a hydrogenated sugar such as those mentioned above. This may be advantageously internal dehydration products of hexitols, in particular of "dianhydrohexitols" or "isohexides" such as isosorbide (1,4-3,6-dianhydrosorbitol), isoidide (1,4-3,6-dianhydroiditol) or isomannide.

The expression "trivalent metal phosphates" for the purpose of the present invention means phosphates of trivalent metal (metal(III) phosphates) selected in the group consisting of boron phosphate, aluminum phosphate, iron phosphate, lanthanum phosphate and cerium phosphate.

The expression "solid catalyst" for the purpose of the present invention has to be understood as water insoluble materials which exist in various amorphous and/or crystalline states.

The expression "yield" for the purpose of the present invention has to be understood as:

yield=(obtained product mass)/(theoretical product mass)=(moles number of obtained product)/(moles number of theoretical product)

The mass of obtained product is the mass synthesized. It is determined by weighing of the obtained product. The theoretical product mass is the mass of product corresponding to a yield of 100%. It must therefore be calculated from the mass of the reactants.

The conversion in % is a measure of the efficiency/activity of the catalyst. It is calculated by the amount of starting material added to the reactor (mol in) minus the amount of starting material found in the product mixture (mol out) divided by the amount of starting material (mol in) times 100.

The selectivity is a measure of the property of a catalyst to direct a reaction to a particular product (obtained product). The expression "selectivity" for the purpose of the present invention has to be understood as:

selectivity=yield/conversion

In this formula, selectivity, yield and conversion are calculated on a molar basis. As an example, in a certain reaction, 90% of substance A is converted (consumed), but only 80% of it is converted to the desired substance B and 20% to undesired by-products, so conversion of A is 90%, selectivity for B 80% and yield of substance B 72% (=90%*80%).

Among the doubly dehydrogenated sugars, isosorbide is currently the one for which the largest number of industrial applications is being developed, or at the very least envisaged. Particularly, they relate to the formation of numerous pharmaceutical compounds, the preparation of food or cosmetic products, the production of plastics and polymers or the production of polyurethane, polycarbonate, polyesters and polyamides.

Acidic media are generally used for dehydrating sugar alcohol substrates to obtain internal dehydration products. Several processes for the production of internal dehydration products are known. All commercialized processes involve the use of concentrated homogeneous acids and organic solvents.

Current processes of internal dehydration of hydrogenated sugar are in liquid phase and carried out in standard batch reactors heated for example by oil in a double-jacket, fitted with a condenser and a receiver for the distillate. The standard conditions are gentle temperatures, e.g. between 100 to 200° C., and under vacuum, e.g. at 20 to 400 mbar. A liquid catalyst, like sulfuric acid $H_2SO_4$ at 1% by weight, is generally used.

This method results in high conversion levels, but requires the use of corrosive and non-reusable homogeneous Brönsted acid catalysts such as $H_2SO_4$. Thus, the need for one-use catalyst and corrosion resistant materials are major disadvantages of this method. Another big disadvantage is the high salt formation due to the neutralization of the homogeneous acids by bases and the costly disposal of those salts.

Alternatively, internal dehydration products can be produced by reacting an aqueous solution of hydrogenated sugar over heterogeneous catalysts. The solid nature of catalysts makes them easy to be removed and recovered from reaction mixtures and thus, to reduce the usage of solvents and environmentally adverse chemicals. Furthermore, there is no expensive working up procedure to get rid of the salt.

Goodwin et al. (*Carbohydrates Res.* 79:133-141, 1980) have disclosed a method involving the use of acidic-cation-exchange resin instead of concentrated, corrosive homogeneous acids, but with low yield of isosorbide synthesis.

U.S. Pat. No. 7,420,067 describes good yield of synthesis of internal dehydration products (about 50%) obtained in the presence of a solid acid catalyst at a temperature of about 150° C. to about 350° C. and under elevated pressure (from about 9 bar to about 140 bar). The solid catalysts used are inorganic ion exchange material selected from the group consisting of acidic ion exchange resins and acidic zeolite powders. However, these solid catalysts have the disadvantages of being not temperature stable in case of ion exchange resins and very expensive in the case of zeolites. In addition the zeolitic catalysts have the tendency to fast deactivation by blocking the pores and covering the acid sides by polymer and coke formation.

Other solid catalysts, such as metal (IV) phosphates, may present good performances for selective catalysis in the formation of mono- and bi-cyclic ethers from diols (Al-Qallaf Fawzia et al., *J Mol Catal A:Chem* 152:187, 2000).

As described in patent applications CN 101492457 and CN 101492458 metal (IV) oxides modified with $H_3PO_4$ and metal (IV) orthophosphates, as tin, zirconium and titanium phosphates, were already tested for selective dehydration of sorbitol to isosorbide in gas-phase. These tetravalent metal phosphates used as catalysts exhibit a good selectivity and a good yield in preparing isosorbide from sorbitol. However, the tetravalent phosphates present the inconvenience to be expensive, because their preparation requires a sequence of energy consuming subsequent processes, e.g. calcinations, refluxing for long times, hydrothermal treatment. More than that, some of them are toxic, such the tin phosphate. Other disadvantages are the high price of the metals such as Zr and Ti.

The objective of the present invention is to develop a simple, low cost, environmentally friendly and sustainable process for the production of internal dehydration products of hydrogenated sugar. This was achieved thanks to a special method implementing a trivalent metal phosphate (metal (III) phosphate) used as a catalyst.

SUMMARY OF THE INVENTION

The present invention relates to a novel method for preparing compositions containing at least one internal dehydration product of hydrogenated sugar, characterized in that it comprises a step of dehydration of a hydrogenated sugar in presence of a solid trivalent metal phosphate catalyst. Specially, the invention concerns a novel method for preparing compositions of dianhydrohexitols.

DETAILED DESCRIPTION OF THE INVENTION

The process according to the invention is related to the use of at least one hydrogenated sugar and dehydrating it in the presence of metal (III) phosphate(s) as catalyst(s) to form a reaction product comprising monoanhydro- and/or dianhydrosugar alcohols and water.

For the purpose of the invention, the hydrogenated sugar used as raw material may especially be sorbitol, mannitol, iditol, galactitol, pentitol or tetritol, in form of aqueous solution or of powder. It may also be a mixture of these hydrogenated sugars. Such hydrogenated sugars may be obtained by any known technique, generally followed by at least one technique for purifying the reaction crude thus obtained.

When hydrogenated sugar is used in the form of an aqueous solution, the aqueous solution contains preferably between 40 wt. % and 98 wt. % of hydrogenated sugar. When hydrogenated sugar is used in powder form, the powder contains preferably more than 98 wt. % of hydrogenated sugar, more preferably more than 99 wt %.

The dehydration of the hydrogenated sugar is carried out in the presence of a trivalent metal phosphate catalyst, used alone or combined with another trivalent metal phosphate catalyst.

The trivalent metal phosphate catalysts are selected from the group consisting of boron phosphate ($BPO_4$), aluminum phosphate ($AlPO_4$), iron phosphate ($FePO_4$), lanthanum phosphate ($LaPO_4$) and cerium phosphate ($CePO_4$). These metal (III) phosphates catalysts are cheaper catalysts compared with catalysts containing Ti and Zr. They are easy to prepare, just by mixing together the metal trioxide with $H_3PO_4$. Moreover, the advantages of using heterogeneous catalysts, e.g. regeneration, no salt formation, cause the proposition of alternative solid acid catalysts for dehydration of hydrogenated sugar.

Preferably, the amount of the catalyst used in the process ranges from 0.5 to 15 wt.-% related to the amount of hydrogenated sugar, more preferably between 1 and 7 wt.-%, and even more preferably between 1 and 3 wt.-%.

The metal phosphates can be used as they are provided by the supplier or they can be calcined or even modified by post treatments such as treatment with acids and/or steam. Different calcination procedures can be used to calcine the catalysts, e.g. at 200° C. for 12 hours, at 400° C. for 8 hours and at 600° C. for 12 hours. The preferred forms of the catalyst are the uncalcined ones.

For the purpose of the present invention, the reaction (i.e. the dehydration step) can be carried out either in batchwise mode or in continuous mode.

For the purpose of the present invention, the reaction can be carried out in the liquid phase or in the gas phase or in the supercritical phase. For the liquid phase reaction it can be used a reactor selected in the group consisting of autoclave type reactors such as stainless steel autoclave equipped with a pressure gauge, or stirred tank reactors (STR), loop reactors, cascade reactor, STRs in series. Regardless, the reaction can be carried out batch wise or continuously.

Furthermore the reaction can be carried out in the liquid phase or gas phase or supercritical phase applying a continuous flow fixed bed tube reactor, a multi tubular reactor, a plate reactor, a short fixed bed reactor allowing very short residence times, a riser reactor, a fluidized bed reactor or a fluidized bed reactor with continuous regeneration in a fixed bed reactor or fluidized bed reactor.

According to a preferred variant of the invention, the dehydration takes place in a stainless steel autoclave containing the hydrogenated sugar, the trivalent metal phosphate catalyst and a magnetic stirrer bar.

Preferably, the stirring is in the range of 400 rpm and 1500 rpm, more preferably between 700 rpm and 1200 rpm.

In a preferred embodiment the autoclave is equipped with a pressure gauge.

The process of preparation of the present invention is preferably conducted in an autoclave type reactor under self-generated pressure. In this case of autogeneous pressure, the pressure is increased by increasing the temperature of the reaction. In the range of 220-290° C., the pressure self-generated inside the reactor is comprised between 1 and 40 bar.

The system can be artificially pressurized prior to heating with a non-reactive gas, preferably nitrogen gas or argon gas or methane gas, or can be depressurized during reaction.

According to a specific variant, the autoclave is flushed one or more times, preferably three times, with a non-reactive gas, preferably nitrogen gas or argon gas.

According to another preferred variant, the autoclave is depressurized for, for example, about 10-15 seconds at the beginning of the dehydration reaction. Preferably, the autoclave is depressurized until no steam was getting out from the autoclave.

According to one variant, the process is conducted under a pressure comprised between 1 and 40 bar, more preferably, the pressure is set to 20 bars.

The heating to the reaction temperature may be provided by an electrical heater equipped with a temperature controller. Preferably, the process of preparation of the present invention is conducted at a temperature of 150° C. to 290° C., preferably 200° C. to 270° C. and more preferably 200° C. to 250° C.

According to a specific variant, the process is conducted in steps: a first step wherein the temperature is set to a lower value, preferably under 200° C., more preferably under 190° C., for example at 180° C., and a second step wherein the temperature is set to a higher value, preferably upper 200° C., more preferably upper 240° C., for example at 250° C.

According to the present invention, the process of dehydration is conducted for 0.5 to 24 hours, preferably for 2 to 8 hours and more preferably for 2 hours. After the given reaction time, the heating device is removed and the autoclave is cooled down to room temperature, for example by immersing into ice bath.

The present invention will be described in greater detail with the aid of the following examples which are not at all limiting.

EXAMPLES

For all the following examples, the reaction mixture is analyzed conventionally by gas chromatography (GC) and the results are presented in Table 1.

Example 1

45.5 g sorbitol powder 100%, 0.46 g of boron phosphate and a magnetic stirrer bar were added in a 75 ml stainless steel autoclave (without glass inlet). The autoclave was sealed and connected to the heating device. The reaction was carried out at 220° C. with stirring (1100 rpm), under self-generated pressure. The reaction was stopped after 2 hours. The heating device was removed and the autoclave was cooled down to room temperature by immersing into ice bath. The reaction mixture was filtered using polyamide syringe filter and analyzed by GC.

Examples 2-6 differing from Example 1 in reaction temperature and reaction time were conducted according to the same procedure as for Example 1.

Example 7 was performed according to the same procedure as for Example 1 with the difference that the reaction was conducted in 2 steps: in the first step the temperature was set to 180° C. for 2 hours and after this the temperature was increased to 250° C. and maintained at this value for other 2 hours.

Example 8

32.3 g sorbitol powder 100%, 0.32 g of boron phosphate and a magnetic stirrer bar were added in a 75 ml stainless steel autoclave (without glass inlet). The autoclave was sealed and connected to the heating device. The reaction was carried out at 200° C. with stirring (1100 rpm), under self-generated pressure. The reaction was stopped after 8 hours. The heating device was removed and the autoclave was cooled down to room temperature by immersing into ice bath. The reaction mixture was filtered using polyamide syringe filter and analyzed by gas chromatography.

Examples 9 and 10 differing from Example 8 in reaction temperature and reaction time were conducted according to the same procedure as for Example 8.

Example 11

32.3 g sorbitol powder 100%, 0.32 g of lanthanum phosphate and a magnetic stirrer bar were added in a 75 ml stainless steel autoclave (without glass inlet). The autoclave was sealed and connected to the heating device. The reaction was carried out at 250° C. with stirring (1100 rpm), under self-generated pressure. The reaction was stopped after 2 hours. The heating device was removed and the autoclave was cooled down to room temperature by immersing into ice bath. The reaction mixture was filtered using polyamide syringe filter and analyzed by gas chromatography.

Example 12 was performed according to the same procedure as for Example 11 with the difference that the catalyst used was cerium phosphate.

Comparative Example 1 was performed according to the same procedure as for Example 11 using a tetravalent phosphate as catalyst-zirconium phosphate.

Comparative Example 2 was performed according to the same procedure as for Example 3 using a tetravalent phosphate as catalyst-titanium phosphate.

TABLE 1

| Example | Conditions of reaction | Sorbitol conversion, % | Isosorbide selectivity, % mol |
|---|---|---|---|
| 1 | 220° C./2 h/sorbitol powder 100%, 45.5 g | 100 | 44.9 |
| 2 | 220° C./8 h/sorbitol powder 100%, 45.5 g | 100 | 52.9 |
| 3 | 250° C./2 h/sorbitol powder 100%, 45.5 g | 99.4 | 52.1 |
| 4 | 250° C./4 h/sorbitol powder 100%, 45.5 g | 99.7 | 54.1 |
| 5 | 270° C./2 h/sorbitol powder 100%, 45.5 g | 100 | 55.3 |
| 6 | 290° C./0.5 h/sorbitol powder 100%, 45.5 g | 100 | 49.8 |
| 7 | 180° C./2 h + 250° C./2 h sorbitol powder 100%, 45.5 g | 100 | 57.7 |
| 8 | 200° C./8 h/sorbitol powder 100%, 32.3 g | 100 | 63 |
| 9 | 220° C./2 h/sorbitol powder 100%, 32.3 g | 100 | 52.3 |
| 10 | 220° C./8 h/sorbitol powder 100%, 32.3 g | 100 | 50.1 |
| 11 | 250° C./2 h/sorbitol powder 100%, 32.3 g | 100 | 54.4 |
| 12 | 250° C./2 h/sorbitol powder 100%, 32.3 g | 100 | 64.4 |
| Comparative 1 | 250° C./2 h/sorbitol powder 100%, 32.3 g | 99.7 | 46.3 |
| Comparative 2 | 250° C./2 h/sorbitol powder 100%, 45.5 g | 99 | 35 |

The invention claimed is:

1. A method for preparing a composition containing dianhydrohexitol, wherein said method comprises
    heating a hexitol in the presence of a solid trivalent metal phosphate catalyst selected from the group consisting of boron phosphate, aluminum phosphate, iron phosphate, lanthanum phosphate and cerium phosphate; and
    thereby performing dehydration of said hexitol into said dianhydrohexitol.
2. The method according to claim 1, wherein the catalyst is uncalcined.

3. The method according to claim 1, wherein said heating the hexitol is conducted at a temperature of 150° C. to 290° C.

4. The method according to claim 1, wherein said heating the hexitol is conducted in 2 steps:
   a. a first step wherein the temperature is set to a temperature under 200° C, and
   b. a second step wherein the temperature is set to a temperature above 200° C.

5. The method according to claim 1, wherein said heating the hexitol is conducted under self-generated pressure.

6. The method according to claim 5, wherein said heating the hexitol is conducted under a pressure set to 1-40 bars.

7. The method according to claim 1, wherein said hexitol is in the form of an aqueous solution.

8. The method according to claim 1, wherein said hexitol is in the form of powder.

9. The method according to claim 1, wherein said heating the hexitol is conducted for 0.5 - 24.

10. The method according to claim 1, wherein said heating the hexitol takes place in an autoclave.

11. The method according to claim 10, wherein prior to said heating the hexitol the autoclave is flushed one or more times, with a non-reactive gas.

12. The method according to claim 10, wherein at the beginning of said heating the hexitol the autoclave is artificially pressurized prior to heating with a non-reactive gas.

13. The method according to claim 12, wherein a step of depressurization of the autoclave is conducted for about 10 - 15 seconds.

14. The method according to claim 13, wherein the step of depressurization is conducted until no steam is escaping from the autoclave.

15. The method according to claim 1 wherein the dehydration of said hexitol is carried out either in batchwise mode or in continuous mode.

16. The method according to claim 1 wherein the dehydration of said hexitol is carried out either in the liquid phase or gas phase or supercritical phase.

17. The method according to claim 1, wherein said heating the hexitol is conducted at a temperature of 200° C to 270° C.

18. The method according to claim 1, wherein said heating the hexitol is conducted for 2 to 8 hours.

19. The method according to claim 12, wherein the non-reactive gas is nitrogen, argon or methane gas.

20. The method according to claim 1, wherein the solid trivalent metal phosphate catalyst is selected from the group consisting of lanthanum phosphate and cerium phosphate.

\* \* \* \* \*